United States Patent
Hershkowitz et al.

(10) Patent No.: US 9,783,463 B2
(45) Date of Patent: Oct. 10, 2017

(54) CONVERSION OF ACETYLENE AND METHANOL TO AROMATICS

(71) Applicant: ExxonMobil Chemical Patents Inc., Baytown, TX (US)

(72) Inventors: Frank Hershkowitz, Basking Ridge, NJ (US); Stephen H. Brown, Lebanon, NJ (US); Paul F. Keusenkothen, Houston, TX (US); Tilman W. Beutel, Neshanic Station, NJ (US); Stephen J. McCarthy, Center Valley, PA (US); Michel Daage, Hellertown, PA (US); Rohit Vijay, Bridgewater, NJ (US); Samia Ilias, Somerville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/829,199

(22) Filed: Aug. 18, 2015

(65) Prior Publication Data

US 2016/0090334 A1  Mar. 31, 2016

Related U.S. Application Data

(60) Provisional application No. 62/057,573, filed on Sep. 30, 2014.

(51) Int. Cl.
*C07C 2/54* (2006.01)
*C07C 2/58* (2006.01)
(Continued)

(52) U.S. Cl.
CPC ............... *C07C 2/864* (2013.01); *C07C 5/35* (2013.01); *C07C 2529/40* (2013.01)

(58) Field of Classification Search
CPC ................ C07C 2/54; C07C 2/58; C07C 5/35
(Continued)

(56) References Cited

U.S. PATENT DOCUMENTS

| 2,158,582 | A | | 5/1939 | Isham et al. | |
| 2,727,932 | A | * | 12/1955 | Evans | C07C 4/025 252/8 |

(Continued)

FOREIGN PATENT DOCUMENTS

| EP | 0 158 975 | 4/1984 |
| EP | 0 158 976 | 4/1985 |

(Continued)

OTHER PUBLICATIONS

U.S. Appl. No. 61/349,464.
S.Ilias, R. Khare, A. Malek, A. Bhan, J. Catal., 303 (2013)135-140.

*Primary Examiner* — Thuan D Dang

(57) ABSTRACT

Methods are provided for forming aromatic compounds from a highly unsaturated aliphatic feeds optionally in combination with methanol. The method can include dehydrogenating a feed containing at least about 50 vol % $C_1$-$C_4$ alkanes under dehydrogenation conditions to form a dehydrogenation effluent containing at least about 25 vol % alkynes. Alternatively, other sources of alkyne-containing feeds can be used. At least a portion of the alkyne-containing feed can then be converted under effective conversion conditions to form a conversion effluent comprising a hydrocarbon product containing aromatic compounds.

11 Claims, 5 Drawing Sheets

(51) Int. Cl.
*C07C 5/35* (2006.01)
*C07C 2/86* (2006.01)

(58) Field of Classification Search
USPC ........ 585/322, 658, 407, 418, 419, 420, 421
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu |
| 3,832,449 A | 8/1974 | Rosinski et al. |
| 3,894,102 A | 7/1975 | Chang et al. |
| 3,894,103 A | 7/1975 | Chang et al. |
| 3,894,104 A | 7/1975 | Chang et al. |
| 3,894,107 A | 7/1975 | Butter et al. |
| 3,928,483 A | 12/1975 | Chang et al. |
| 3,960,978 A | 6/1976 | Givens et al. |
| 4,016,245 A | 4/1977 | Plank et al. |
| 4,021,502 A | 5/1977 | Plank et al. |
| 4,025,571 A | 5/1977 | Lago |
| 4,035,430 A | 7/1977 | Dwyer et al. |
| 4,046,685 A | 9/1977 | Bray |
| 4,049,573 A | 9/1977 | Kaeding |
| 4,058,576 A | 11/1977 | Chang et al. |
| 4,076,842 A | 2/1978 | Plank et al. |
| 4,079,095 A | 3/1978 | Givens et al. |
| 4,088,706 A | 5/1978 | Kaeding |
| RE29,948 E | 3/1979 | Dwyer et al. |
| 4,150,062 A | 4/1979 | Garwood et al. |
| 4,211,640 A | 7/1980 | Garwood et al. |
| 4,227,992 A | 10/1980 | Garwood et al. |
| 4,310,440 A | 1/1982 | Wilson et al. |
| 4,397,827 A | 8/1983 | Chu |
| 4,417,780 A | 11/1983 | Knapp |
| 4,423,274 A | 12/1983 | Daviduk et al. |
| 4,424,401 A | 1/1984 | White et al. |
| 4,433,185 A | 2/1984 | Tabak |
| 4,433,189 A | 2/1984 | Young |
| 4,440,871 A | 4/1984 | Lok et al. |
| 4,445,031 A | 4/1984 | Kamoshida |
| 4,456,779 A | 6/1984 | Owen et al. |
| 4,476,338 A | 10/1984 | Chang et al. |
| 4,500,651 A | 2/1985 | Lok et al. |
| 4,547,616 A | 10/1985 | Avidan et al. |
| 4,551,236 A | 11/1985 | Lok et al. |
| 4,554,143 A | 11/1985 | Messina et al. |
| 4,556,477 A | 12/1985 | Dwyer |
| 4,567,029 A | 1/1986 | Wilson et al. |
| 4,579,999 A | 4/1986 | Gould et al. |
| 4,605,492 A | 8/1986 | Lok et al. |
| 4,654,455 A | 3/1987 | Chao |
| 4,683,217 A | 7/1987 | Lok et al. |
| 4,684,617 A | 8/1987 | Lok et al. |
| 4,686,092 A | 8/1987 | Lok et al. |
| 4,686,093 A | 8/1987 | Flanigen et al. |
| 4,735,806 A | 4/1988 | Flanigen et al. |
| 4,737,353 A | 4/1988 | Flanigen et al. |
| 4,738,837 A | 4/1988 | Flanigen et al. |
| 4,744,885 A | 5/1988 | Messina et al. |
| 4,744,970 A | 5/1988 | Lok et al. |
| 4,746,763 A | 5/1988 | Kocal |
| 4,751,338 A | 6/1988 | Tabak et al. |
| 4,758,419 A | 7/1988 | Lok et al. |
| 4,759,919 A | 7/1988 | Flanigen et al. |
| 4,781,814 A | 11/1988 | Flanigen et al. |
| 4,793,833 A | 12/1988 | Lok et al. |
| 4,793,984 A | 12/1988 | Lok et al. |
| 4,801,309 A | 1/1989 | Lok et al. |
| 4,801,364 A | 1/1989 | Wilson et al. |
| 4,822,478 A | 4/1989 | Lok et al. |
| 4,824,554 A | 4/1989 | Lok et al. |
| 4,846,956 A | 7/1989 | Lok et al. |
| 4,853,197 A | 8/1989 | Wilson et al. |
| 4,880,520 A | 11/1989 | Lok et al. |
| 4,882,038 A | 11/1989 | Lok et al. |
| 4,917,876 A | 4/1990 | Lok et al. |
| 4,935,216 A | 6/1990 | Lok et al. |
| 4,940,570 A | 7/1990 | Flanigan et al. |
| 4,952,384 A | 8/1990 | Lok et al. |
| 4,956,164 A | 9/1990 | Lok et al. |
| 4,956,165 A | 9/1990 | Lok et al. |
| 4,973,785 A | 11/1990 | Lok et al. |
| 5,057,295 A | 10/1991 | Flanigan et al. |
| 5,241,093 A | 8/1993 | Joly et al. |
| 5,345,011 A | 9/1994 | Durante et al. |
| 5,434,326 A | 7/1995 | Gajda et al. |
| 5,475,182 A | 12/1995 | Janssen |
| 5,478,787 A | 12/1995 | Dandekar et al. |
| 5,493,066 A | 2/1996 | Kraushaar-Czarnetzki et al. |
| 5,675,050 A | 10/1997 | Des Courieres et al. |
| 5,879,655 A | 3/1999 | Miller et al. |
| 5,925,586 A | 7/1999 | Sun |
| 5,925,800 A | 7/1999 | Sun et al. |
| 5,932,512 A | 8/1999 | Sun |
| 5,962,762 A | 10/1999 | Sun et al. |
| 6,005,155 A | 12/1999 | Sun |
| 6,046,373 A | 4/2000 | Sun |
| 6,051,746 A | 4/2000 | Sun et al. |
| 6,153,552 A | 11/2000 | Wachter et al. |
| 6,156,931 A | 12/2000 | Lewis |
| 6,225,254 B1 | 5/2001 | Janssen et al. |
| 6,372,949 B1 | 4/2002 | Brown et al. |
| 6,521,562 B1 | 2/2003 | Clem et al. |
| 7,491,250 B2 | 2/2009 | Hershkowitz et al. |
| 7,846,401 B2 | 12/2010 | Hershkowitz et al. |
| 7,943,808 B2 | 5/2011 | Hershkowitz et al. |
| 2002/0055433 A1 | 5/2002 | Fung et al. |
| 2002/0115897 A1 | 8/2002 | Janssen et al. |
| 2007/0144940 A1 | 6/2007 | Hershkowitz et al. |
| 2007/0191664 A1 | 8/2007 | Hershkowitz et al. |
| 2008/0142409 A1 | 6/2008 | Sankaranarayanan et al. |
| 2011/0291051 A1* | 12/2011 | Hershkowitz .......... B01J 8/0453 252/373 |
| 2013/0251608 A1 | 9/2013 | Chun et al. |
| 2015/0158787 A1* | 6/2015 | Henao ...................... C07C 2/58 585/324 |

FOREIGN PATENT DOCUMENTS

| | | |
|---|---|---|
| EP | 0 159 624 | 10/1985 |
| EP | 0 161 489 | 11/1985 |
| EP | 0 293 937 | 12/1988 |
| WO | 96/10547 | 4/1996 |
| WO | 01/25151 | 4/2001 |
| WO | 01/36329 | 5/2001 |
| WO | 01/60746 | 8/2001 |
| WO | 2013/165655 | 11/2013 |

* cited by examiner

CONVERSION OF ACETYLENE AND METHANOL TO AROMATICS

PRIORITY CLAIM

This application claims priority to and the benefit of U.S. Provisional Application No. 62/057,573, filed Sep. 30, 2014, the disclosure of which is incorporated herein by reference in its entirety.

FIELD OF THE INVENTION

Methods are provided for the manufacture of aromatics from feeds containing acetylene.

BACKGROUND OF THE INVENTION

Conversion of various feeds to aromatic compounds is an industrially valuable process. Some conventional methods can allow for conversion of light alkanes. For example, a feed including light alkanes can be exposed to a combination of a dehydrogenation step and a cyclization/aromatization step to produce aromatics. Examples of such a process are described in U.S. Pat. Nos. 4,654,455 and 4,746,763. Unfortunately, the dehydrogenation process typically requires elevated temperatures while the cyclization/aromatization step prefers lower temperatures. As a result, the combination dehydrogenation and aromatization processes typically involve low conversion and extensive recycle, which increases the overall cost of producing the aromatics.

Other conventional methods for forming aromatics can include conversion of methanol and/or olefins to aromatics in the presence of a molecular sieve, such as ZSM-5. Reactions for conversion of methanol and/or olefins to aromatics can be useful, for example, for creation of aromatics as individual products, or for formation of aromatic and olefin mixtures for use as naphtha boiling range or distillate boiling range fuels.

U.S. Pat. Nos. 4,049,573 and 4,088,706 disclose that methanol can be converted to a hydrocarbon mixture rich in $C_2$-$C_3$ olefins and mononuclear aromatics, particularly p-xylene, by contacting the methanol at a temperature of 250-700° C. and a pressure of 0.2 to 30 atmospheres with a crystalline aluminosilicate zeolite catalyst which has a Constraint Index of 1-12 and which has been modified by the addition of an oxide of boron or magnesium either alone or in combination or in further combination with oxide of phosphorus. The above-identified disclosures are incorporated herein by reference.

Methanol can be converted to gasoline employing the MTG (methanol to gasoline) process. The MTG process is disclosed in the patent art, including, for example, U.S. Pat. Nos. 3,894,103; 3,894,104; 3,894,107; 4,035,430 and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10}+$ olefin precursors of the desired distillate are rapidly converted via hydrogen transfer to heavy polymethylaromatics and $C_4$ to $C_8$ isoparaffins under methanol conversion conditions.

One side reaction in conversion of methanol to gasoline is the formation of durene, which is a tetramethylated aromatic. Due to a unexpectedly high melting point, excess formation of durene can be less desirable during formation of gasoline. U.S. Pat. No. 4,476,338 describes one alternative for reducing or minimizing formation of durene during conversion of methanol to gasoline.

Olefinic feedstocks can also be used for producing $C_5+$ gasoline, diesel fuel, etc. In addition to the basic work derived from ZSM-5 type zeolite catalysts, a number of discoveries contributed to the development of the industrial process known as Mobil Olefins to Gasoline/Distillate ("MOGD"). This process has significance as a safe, environmentally acceptable technique for utilizing feedstocks that contain lower olefins, especially $C_2$ to $C_5$ alkenes. In U.S. Pat. Nos. 3,960,978 and 4,021,502, Plank, Rosinski and Givens disclose conversion of $C_2$ to $C_5$ olefins alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over ZSM-5 is effective at moderately elevated temperatures and pressures. The conversion products are sought as liquid fuels, especially the $C_5+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in U.S. Pat. Nos. 4,445,031, 4,456,779, Owen et al, and U.S. Pat. No. 4,433,185, Tabak, incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process (MTO) for converting low cost methanol to valuable hydrocarbons rich in ethene and $C_3+$ alkenes. Various processes are described in U.S. Pat. No. 3,894,107 (Batter et al), U.S. Pat. No. 3,928,483 (Chang et al), U.S. Pat. No. 4,025,571 (Lago), U.S. Pat. No. 4,423,274 (Daviduk et al) and U.S. Pat. No. 4,433,189 (Young), incorporated herein by reference. It is generally known that the MTO process can be optimized to produce a major fraction of $C_2$ to $C_4$ olefins. Prior process proposals have included a separation section to recover ethene and other gases from by-product water and $C_5+$ hydrocarbon liquids. The oligomerization process conditions which favor the production of $C_{10}$ to $C_{20}$ and higher aliphatics tend to convert only a small portion of ethene as compared to $C_3+$ olefins.

The methanol to olefin process (MTO) operates at high temperature and near 30 psig in order to obtain efficient conversion of the methanol to olefins. These process conditions, however, produce an undesirable amount of aromatics and $C_2$ olefins and require a large investment in plant equipment.

The olefins to gasoline and distillate process (MOGD) operates at moderate temperatures and elevated pressures to produce olefinic gasoline and distillate products. When the conventional MTO process effluent is used as a feed to the MOGD process, the aromatic hydrocarbons produced in the MTO unit are desirably separated and a relatively large volume of MTO product effluent has to be cooled and treated to separate a $C_2-$ light gas stream, which is unreactive, except for ethene which is reactive to only a small degree, in the MOGD reactor, and the remaining hydrocarbon stream has to be pressurized to the substantially higher pressure used in the MOGD reactor.

Reverse flow reactors are well-suited for performing endothermic reactions that are facilitated by high temperature environments. U.S. Pat. No. 7,846,401 describes an example of a regenerative bed reverse flow reactor system, which is incorporated herein by reference. The reactor system is described as being suitable for a variety of pyrolysis reactions, such as hydropyrolysis of methane to form acetylene.

U.S. Pat. No. 6,372,949 describes methods for converting an oxygenate feed to gasoline or distillate boiling range compounds by exposing the oxygenate feed to a catalyst including a 10-member ring zeolite. The methods can optionally convert the oxygenate feed in the presence of a $C_4+$ olefin co-feed which is described as improving the selectivity for formation of distillate boiling range compounds. An example of a suitable co-feed is described as a recycled cut of naphtha that is rich in heavy olefins, such as pentenes, hexenes, and heptenes. The Examples and Comparative Examples are directed to a comparison of conversion of a methanol feed relative to conversion of a feed containing 90 wt. % methanol and 10 wt. % hexene.

There is an ongoing desire to improve methods of converting methanol to aromatics that yield a higher amount of aromatics than prior art methods.

SUMMARY OF THE INVENTION

The present invention provides methods for converting hydrocarbons, such as alkanes, alkenes and/or alkynes, particularly acetylene, to aromatics. In some embodiments, methanol is co-fed with the hydrocarbons to increase the amount of xylenes formed.

In one aspect, a feed containing at least about 50 vol % $C_1$-$C_4$ alkanes is dehydrated under dehydrogenation conditions to form a dehydrogenation effluent containing at least about 25 vol % alkynes. The dehydrogenation conditions include a temperature of at least about 1000° C. At least a portion of the dehydrogenation effluent is then converted under effective conversion conditions to form a conversion effluent comprising a hydrocarbon product containing aromatic compounds, a volume percentage of aromatic compounds in the hydrocarbon product being at least about 10 vol % greater than a volume percentage of aromatic compounds in the at least a portion of the dehydrogenation effluent. Optionally, the feed containing at least about 50 vol % $C_1$-$C_4$ alkanes can be a feed containing at least about 75% $C_2$ alkanes, or at least about 75% $C_1$-$C_2$ alkanes. The dehydrogenation conditions can correspond to pyrolysis conditions or partial oxidation conditions.

In another aspect an acetylene-containing effluent containing at least about 50 vol % acetylene is formed by exposing calcium carbide to water under effective conditions for forming acetylene. At least a portion of the acetylene-containing effluent is converted under effective conversion conditions to form a conversion effluent comprising a hydrocarbon product containing aromatic compounds, a volume percentage of aromatic compounds in the hydrocarbon product being at least about 10 vol % greater than a volume percentage of aromatic compounds in the at least a portion of the acetylene-containing effluent.

In still another aspect, a method for converting oxygenates to aromatics is provided, including exposing an oxygenate feed to an aromatization catalyst comprising ZSM-5 under effective conversion conditions to form a conversion effluent comprising aromatics. The oxygenate feed has a ratio of carbon atoms in oxygenates to carbon atoms in $C_3$-$C_{10}$ olefins of 10:90 to 95:5. Optionally, the oxygenate feed can have a ratio of carbon atoms in oxygenates to carbon atoms in $C_3$-$C_5$ olefins of about 5.5:1 to about 1:5, or a ratio of carbon atoms in oxygenates to carbon atoms in $C_4$-$C_7$ olefins of about 5.5:1 to about 1:5.

The aromatization catalyst utilized comprises a molecular sieve, preferably ZSM-5, and at least one Group 8-14 element. Effective conversion conditions include a temperature of about 350° C. to about 700° C., a pressure of about 100 kPaa to about 7000 kPaa, and a weight hourly space velocity of about 0.1 $hr^{-1}$ to about 20 $hr^{-1}$. The claimed methods provide an increase yield of aromatics, particularly xylenes, as compared to prior art methods.

DETAILED DESCRIPTION OF THE EMBODIMENTS

Overview

Figure 1:
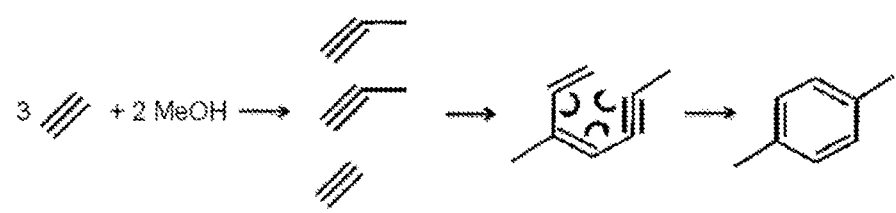
FIG. 1 shows an example of a possible reaction mechanism for conversion of acetylene and methanol to para-xylene.

In various aspects, methods are provided for efficient conversion of light paraffins to aromatics, such as para-xylene or other xylenes. An initial reaction step is used to convert light paraffins to acetylene. The resulting acetylene product is then used, optionally with added methanol, for synthesis of aromatics. Due to the comparable hydrogen to carbon ratio of acetylene and simple aromatics such as benzene, use of acetylene as a substantial portion of a feed for aromatics formation can reduce or minimize the co-production of light paraffins. Additionally, by performing an initial acetylene conversion, other side products from the acetylene conversion can be beneficially used to allow for integration with other processes.

In other aspects, methods are provided for incorporating olefins into a methanol to aromatics synthesis process to reduce or minimize the production of durene. For example, introduction of pentene into a methanol to aromatics process can reduce the formation of aromatic compounds having three or more alkyl side groups. This benefit in reduction of highly substituted aromatics can be achieved while maintaining an expected yield of desirable aromatics such as xylenes.

The discussion below includes the following sections: I) Conversion Conditions for Formation of Aromatics from Alkynes and/or Oxygenates; II) Catalyst for Conversion of Alkynes and/or Oxygenates; III) Acetylene Formation (Dehydrogenation of Paraffins to Acetylene); IV) Process Flow Examples—Alkynes to Aromatics; and V) Alternative Feeds—Conversion of Mixtures of Oxygenates and Olefins.

I) Conversion Conditions for Formation of Aromatics from Alkynes and/or Oxygenates One option for performing an alkynes to aromatics conversion reaction (or an oxygenate to aromatics conversion reaction), can be to use a moving or fluid catalyst bed with continuous oxidative regeneration. The extent of coke loading on the catalyst can then be continuously controlled by varying the severity and/or the frequency of regeneration. In a turbulent fluidized catalyst bed the conversion reactions are conducted in a vertical reactor column by passing hot reactant vapor upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion. Preferred fluid bed reactor systems are described in Avidan et al. (U.S. Pat. No. 4,547,616); Harandi et al. (U.S. Pat. No. 4,751,338); and Tabak et al. (U.S. Pat. No. 4,579,999), each of which is incorporated herein by reference in its entirety. In other aspects, other types of reactors can be used, such as fixed bed reactors, riser reactors, fluid bed reactors, and/or moving bed reactors.

A suitable feed containing highly unsaturated aliphatic compounds and/or oxygenates can be converted to aromatics by exposing the feed to an aromatization catalyst (as further described below) under effective conversion conditions. General conversion conditions include a pressure of about 100 kPaa to about 7000 kPaa, or about 100 kPaa to about 2000 kPaa, or about 100 kPaa to about 1500 kPaa, or about 100 kPaa to about 1200 kPaa. The amount of feed (weight) relative to the amount of catalyst (weight) can be expressed as a weight hourly space velocity (WHSV). Suitable weight hourly space velocities include a WHSV of about 0.1 $hr^{-1}$ to about 20 $hr^{-1}$, or about 1.0 $hr^{-1}$ to about 10 $hr^{-1}$. A wide range of temperatures can be suitable, depending on the desired type of aromatics-containing product. Thus, temperatures of about 300° C. to about 700° C., or about 300° C. to about 600° C., or about 300° C. to about 500° C., or about 350° C. to about 500° C., or about 300° C. to about 450° C., or about 400° C. to about 600° C. can be suitable. It is noted that the lower temperature ranges are sometimes associated with conversion of oxygenate feeds to gasoline, while the higher temperature ranges are sometimes associated with alkylation (conversion) of benzene or toluene to more highly substituted aromatics, such as xylene.

As an example of the suitability of using highly unsaturated feeds for conversion to aromatics, Table 1 below provides the composition of a feed and a resulting product from a conversion reaction. The feed was exposed to a suitable aromatization catalyst (ZSM-5) under conditions suitable for conversion of toluene and methanol to xylene, such as a temperature of about 500° C., a pressure of about 1000 KPa, and a space velocity of about 1 $hr^{-1}$ to about 8 $hr^{-1}$. For a feed containing a toluene to methanol ratio of about 2:3, these conditions are typically suitable for conversion of about 100% of the methanol and about 30% of the toluene to form aromatics. In the example shown in Table 1, these conditions were used for conversion of a steam cracked effluent that was formed by steam cracking of a vacuum gas oil feed. As shown in Table 1, under the reaction conditions, the ethylene in the steam cracked effluent substantially did not react in the presence of the aromatization catalyst. Some reaction of larger olefins (including propylene) was observed. However, substantially all of the diene and triene compounds in the feed were converted to products. In particular, xylenes were formed as a substantial part of the product, in spite of the absence of xylenes in the original feed.

TABLE 1

Conversion of Steam Cracked VGO to Aromatics

|  | Feed | Product |
| --- | --- | --- |
| Ethylene | 18.0% | 18.0% |
| Propylene | 9.3% | 7.5% |
| Butadienes | 3.6% | 0.0% |
| Other Dienes and Trienes | 3.0% | 0.0% |
| $C_4$+ Olefins | 4.0% | 1.2% |
| Others | 62.1% | 54.3% |
| P-xylene-rich xylenes | 0.0% | 18.0% |

As shown in Table 1, highly unsaturated aliphatic compounds can be converted to aromatics at reaction conditions that result in reduced or minimal amounts of conversion of ethylene and/or propylene. Larger olefins are also only partially converted under the conditions. Although the above example demonstrates substantially complete conversion of diene compounds, it is believed that other highly unsaturated aliphatic compounds such as alkynes can be converted to aromatics under conditions with similar severity.

If a feed substantially composed of alkynes is available, such a feed can be suitable for use in a conversion process for formation of aromatics. More typically, an alkyne-containing feed will also contain at least some olefins. In various aspects, for a feed that contains both alkynes and alkenes, the ratio of alkynes (such as acetylene) to alkenes introduced into a reactor for formation of aromatics can be at least about 1:5, such as about 20:1 to about 1:5. Preferably, the molar ratio of acetylene (or other alkynes) to alkenes can be about 10:1 or less, or about 5:1 or less, or about 3:1 or less, and/or at least about 1:1, or at least about 1:2, or at least about 1:3. It is noted that each upper (lower) bound for the acetylene to methanol ratio is explicitly contemplated with each lower (upper) bound, including the upper bound of having a feed that is substantially composed of acetylene and/or other alkynes. A feed that is substantially composed of acetylene (and/or other alkynes) is defined as a feed where at least about 90 mol % of the aliphatic hydrocarbons are acetylene (and/or other alkynes), or at least about 95 mol %, or at least about 98 mol %, or at least about 99 mol %.

Depending on the aspect, the conditions for the conversion reaction can be selected to control the amount of ethylene (and/or other alkenes) that is incorporated into the aromatic products. In aspects involving lower temperatures and/or lower pressures, ethylene present in the feed to the conversion reaction can pass through the reaction zone with a reduced or minimized amount of reaction. For example, the reaction conditions can be selected so that less than about 50 wt. % of the ethylene present in the feed is reacted under the conversion conditions, or less than about 25 wt. % of the ethylene, or less than about 15 wt. %, or less than about 10 wt. %, or less than about 5 wt. %, or less than about 1 wt. %. In other aspects, at least a portion of the ethylene present in a feed can react under the conversion conditions, such as at least about 25 wt. % of the ethylene in the feed, or at least about 50 wt. %, or at least about 60 wt. %, or at least about 70 wt. %. It is noted that due to the higher hydrogen content of ethylene, if a substantial portion of alkenes are used in aromatic formation, additional unsaturated products and/or hydrogen will also be produced. As a result, reaction of at least about 50 wt. % of the ethylene in a feed may not result in incorporation of at least 50 wt. % of the ethylene into an aromatic product. Instead, a portion of the ethylene can be incorporated into saturated products such as ethane.

In other aspects, the reaction conditions can be selected so that less than about 50 wt. % of the alkenes present in the feed are reacted under the conversion conditions, or less than about 25 wt. % of the alkenes, or less than about 15 wt. %, or less than about 10 wt. %, or less than about 5 wt. %, or less than about 1 wt. %. In other aspects, at least a portion of the alkenes present in a feed can react under the conversion conditions, such as at least about 25 wt. % of the alkenes in the feed, or at least about 50 wt. %, or at least about 60 wt. %, or at least about 70 wt. %. In still other aspects, the reaction conditions can be selected so that less than about 50 wt. % of the $C_2$-$C_4$ alkenes present in the feed are reacted under the conversion conditions, or less than about 25 wt. % of the $C_2$-$C_4$ alkenes, or less than about 15 wt. %, or less than about 10 wt. %, or less than about 5 wt. %, or less than about 1 wt. %. In other aspects, at least a portion of the $C_2$-$C_4$ alkenes present in a feed can react under the conversion conditions, such as at least about 25 wt. % of the $C_2$-$C_4$ alkenes in the feed, or at least about 50 wt. %, or at least about 60 wt. %, or at least about 70 wt. %. In yet other aspects, the reaction conditions can be selected so that less than about 50 wt. % of the $C_2$-$C_3$ alkenes present in the feed are reacted under the conversion conditions, or less than about 25 wt. % of the $C_2$-$C_3$ alkenes, or less than about 15 wt. %, or less than about 10 wt. %, or less than about 5 wt. %, or less than about 1 wt. %. In other aspects, at least a portion of the $C_2$-$C_3$ alkenes present in a feed can react under the conversion conditions, such as at least about 25 wt. % of the $C_2$-$C_3$ alkenes in the feed, or at least about 50 wt. %, or at least about 60 wt. %, or at least about 70 wt. %. It is noted that due to the higher hydrogen content of alkenes, if a substantial portion of alkenes are used in aromatic formation, additional unsaturated products and/or hydrogen will also be produced. As a result, reaction of at least about 50 wt. % of the alkenes in a feed may not result in incorporation of at least 50 wt. % of the alkenes into an aromatic product. Instead, a portion of the alkenes can be incorporated into saturated products such as alkanes.

In aspects where conversion reaction conditions are selected that reduce or minimize the amount of conversion of ethylene (or other small alkene) molecules during formation of aromatics, the unreacted ethylene can form part of the effluent from the conversion reaction. The unreacted ethylene (and/or other small alkenes) can optionally be separated out as a separate product, such as for eventual use in polymer production, or can be recycled to a dehydrogenation reactor and/or the conversion reactor.

In aspects where production of substituted aromatics such as para-xylene is desired, addition of methanol to the conversion reaction can improve the yield of para-xylene. Due to the presence of additional methyl groups, the ratio of hydrogen to carbon in xylene is higher than the corresponding ratio in benzene or acetylene. Adding methanol to the feed stream for the conversion reaction to form aromatics can increase the hydrogen to carbon ratio in the feed to more closely match the ratio for xylene. For example, FIG. 1 shows a simplified reaction mechanism for forming para-xylene from acetylene and methanol. As shown in FIG. 1, two methanol molecules are reacted with two acetylene molecules to form methyl acetylene (additional side product of water for stoichiometric balance not shown). An additional acetylene can then be combined with the methyl acetylene molecules to form the para-xylene backbone. It is noted that other reaction mechanisms can and likely also occur, such as initial formation of benzene or toluene followed by methylation to produce xylene. More generally, without being bound by any particular theory, it is believed that suitable molecular sieves, such as ZSM-5 or other 10-member ring molecular sieves, can rearrange carbon-carbon and carbon-hydrogen bonds with feed molecules to create products having similar hydrogen to carbon ratios as the feed. Thus, it is not believed to be necessary to have feed components that can be assembled in a particular manner in order to form a desired aromatic.

The simplified reaction mechanism shown in FIG. 1 suggests that acetylene to methanol ratios of about 3:2 can be effective for providing a desirable ratio of hydrogen to carbon for xylene formation. More generally, a variety of acetylene to methanol ratios can be used for aromatic formation. For example, the molar ratio of acetylene to methanol in the feed (or co-feeds) to a conversion reaction zone can be from about 10:1 to about 1:10. Preferably, the molar ratio of acetylene to methanol can be about 5:1 or less, or about 3:1 or less, and/or at least about 1:1, or at least about 1:2. It is noted that each upper (lower) bound for the acetylene to methanol ratio is explicitly contemplated with each lower (upper) bound.

As an alternative to or in addition to use of methanol as a co-feed, the aromatization catalyst can also be selectivated to increase the resulting yield of xylenes (such as para-xylene) from a conversion reaction. Selectivation can be achieved by a) catalyst modification, such as Si selectivation with a compound such as a tetraethylorthosilicate; or b) steaming, acid-base washing, or other treatments that can modify the pore-size distribution of the catalyst. Additionally or alternatively, the yield of xylenes (such as para-xylene) can be enhanced by adjustment of the methanol/olefin ratio and/or other process condition optimization.

As an example, various types of feeds can be converted using a conversion process. The conversion processes described herein can be used for conversion of an alkyne-containing feed, optionally with a methanol co-feed, for formation of aromatics. The conversion processes described herein can also be used for conversion of a methanol (or other oxygenate) feed with an olefin co-feed.

During a conversion process, a feed comprising alkynes (and optionally a methanol co-feed), or a feed comprising methanol, dimethyl ether, or a combination thereof can be introduced into a reactor containing an aromatization catalyst. Steam can optionally also be introduced into the reactor. A conversion reaction is then performed to form aromatics, either as an distinct product (such as para-xylene) or as part of a gasoline-type product. After performing the conversion reaction, the reactor effluent can be quenched to facilitate separation of the effluent. The quench can be sufficient to allow removal of water from the effluent as a liquid. Light organics containing 4 carbons or less are removed as a gas phase stream. Ethylene and propylene can subsequently be separated from this light ends stream. The remaining portion of the effluent can substantially correspond to hydrocarbons that are liquids at standard temperature and pressure. If a gasoline is the desired product, no further separation may need to be performed. If a separated aromatics product is desired, a series of separations can then be performed to separate out desired products. For example, a first separation on the liquid effluent can separate C7− (lower boiling) compounds from C8+(higher boiling) compounds. In the first separation, para-xylene and other C8+ molecules are included in the higher boiling fraction, while C7− compounds (benzene, toluene) and other lower boiling compounds such as oxygenates form the lower boiling fraction. In this discussion, a C7− product stream is defined as a product stream where at least 50 wt. % of the hydrocarbons correspond to hydrocarbons having 7 carbons or less. Similarly, a C8+ product stream is defined as a product stream where at least 50 wt. % of the hydrocarbons correspond to hydrocarbons having at least 8 carbons. This lower boiling fraction may also contain a variety of non-aromatic compounds. The lower boiling compounds from this first separation are one suitable source, if desired, for a recycle stream to provide hydrogen-lean molecules to the conversion reaction.

The C8+ fraction can then be further separated into a C8 fraction and a C9+ fraction. The C9+ fraction will typically be primarily aromatics and is another suitable fraction for recycle, if desired. In this discussion, a C8 product stream is defined as a product stream where at least 50 wt. % of the hydrocarbons correspond to hydrocarbons having 8 carbons. Similarly, a C9+ product stream is defined as a product stream where at least 50 wt. % of the hydrocarbons correspond to hydrocarbons having at least 9 carbons. In some aspects, if a distillation column is used, the first separation and second separation can be combined to form the C7−, C8, and C9+ fractions in a single distillation or fractionation process. In some aspects, the separations to form the C7−, C8, and C9+ fractions can correspond to any convenient number of distillation steps in order to improve recovery of the desired C8 fraction.

The C8 fraction of the liquid effluent from conversion will typically include at least a portion of xylene isomers other than para-xylene. The ortho- and meta-xylene isomers can be separated from the para-xylene isomers by any convenient method, such as by using crystallization to separate the isomers or by selective adsorption. Optionally, the C8 fraction can be treated in a xylene isomerization unit prior to recovery of the para-xylene. This can increase the concentration of para-xylene in the C8 fraction relative to the concentration prior to the xylene isomerization. Optionally, the separated ortho- and meta-xylenes can be recycled back to the distillation step(s) for further recovery of any remaining para-xylene and/or for further isomerization to form more para-xylene.

Figure 3:
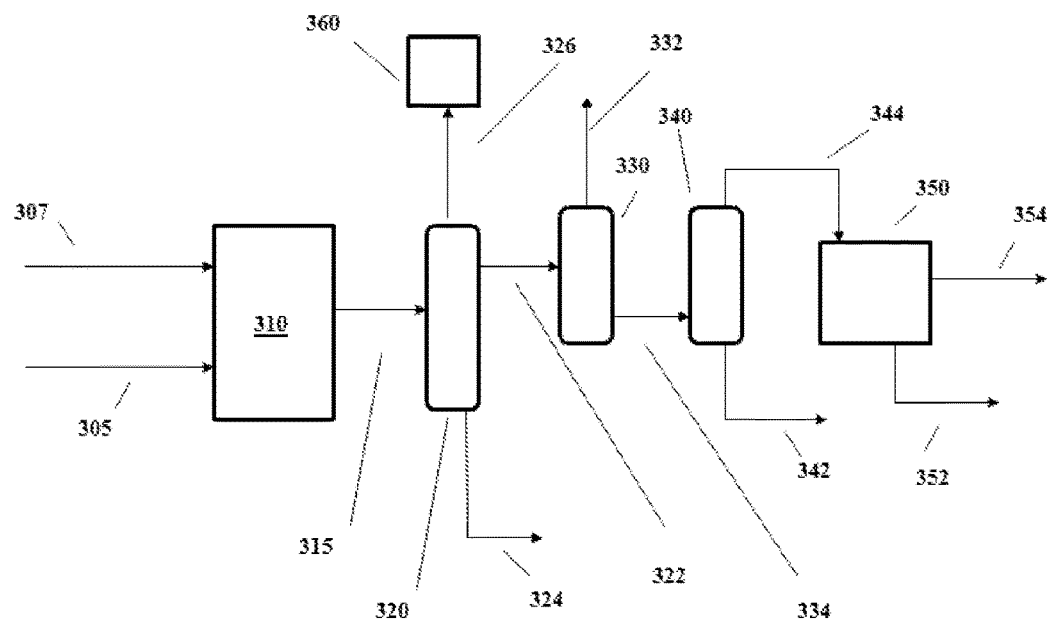
FIG. 3 schematically shows an example of a reaction system for converting a feed to form aromatics.

FIG. 3 shows an example of a reaction system for converting an alkyne-containing feed to aromatics. It is noted that a similar configuration can be used for conversion of methanol to gasoline, with the subsequent separation stages being optional. In FIG. 3, an alkyne-containing feed 305 is introduced into a conversion reactor 310. The reactor 310 can be a fixed bed reactor, a fluidized bed reactor, a riser reactor, or another convenient type of reactor. An optional stream of methanol 307 is also shown in FIG. 3 as being introduced into the reactor.

The total effluent 315 from the conversion reactor 310 can then be passed into a quench stage 320 for separation based on phases of the effluent. Water 324 can be separated out as one liquid phase, while a liquid hydrocarbon effluent 322 can correspond to a second liquid phase. Lower boiling hydrocarbons are removed as a gas phase or light ends stream 326. The light ends stream 326 typically includes ethylene and/or propylene, which can be recovered 360 in one or more recovery processes.

The liquid hydrocarbon effluent 322 is then separated in one or more distillation steps to recover a C8 portion of the effluent (i.e., a C8 product stream). Any convenient number of distillations may be performed. In FIG. 3, the distillation(s) are schematically represented as corresponding to two distillation steps for ease of understanding. A first distillation stage 330 can form a C7− stream 332 and a C8+ stream 334. The C8+ stream 334 is then separated in a second distillation stage 340 to form a C9+ stream 342 and a C8 stream 344. The C8 stream 344 can then be separated 350, such as by crystallization, to separate para-xylene stream 354 from the other xylene isomers 352.

II) Catalyst for Conversion of Alkenes and/or Oxygenates

In various aspects, the catalyst used herein for conversion of alkynes to aromatics and/or for conversion of oxygenates and olefins to aromatics can be a composition of matter comprising a molecular sieve, such as ZSM-5. Optionally, the composition of matter can include a Group 8-14 element, or a combination of metals from the same group of the Periodic Table. The composition of matter can optionally further comprise phosphorus and/or lanthanum and/or other elements from Group 1-2 and/or Group 13-16 of the Periodic Table that provide structural stabilization. In this sense, the term "comprising" can also mean that the catalyst can comprise the physical or chemical reaction product of the molecular sieve and the Group 8-14 element or combination of elements from the same group (and optionally phosphorus and/or lanthanum and/or other elements from groups 1-2 and/or group 13-16). In this description, reference to a group number for an element corresponds to the current IUPAC numbering scheme for the periodic table. Optionally, the catalyst may also include a filler or binder and may be combined with a carrier to form slurry.

In various aspects, the molecular sieve comprises ≥10.0 wt. % of the catalyst, such about 10.0 to 100.0 wt. %, preferably about 25.0 to 95.0 wt. %, and more preferably about 50.0 to 90.0 wt. %.

As used herein the term "molecular sieve" refers to crystalline or non-crystalline materials having a porous structure. Microporous molecular sieves typically have pores having a diameter of ≤about 2.0 nm. Mesoporous molecular sieves typically have pores with diameters of about 2 to about 50 nm. Macroporous molecular sieves have pore diameters of >50.0 nm.

Particular molecular sieves are zeolitic materials. Zeolitic materials are crystalline or para-crystalline materials. Some zeolites are aluminosilicates comprising [SiO4] and [AlO4] units. Other zeolites are aluminophosphates (AlPO) having structures comprising [AlO4] and [PO4] units. Still other zeolites are silicoaluminophosphates (SAPO) comprising [SiO4], [AlO4], and [PO4] units.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

Additionally or alternatively, the molecular sieves useful herein may be characterized by a ratio of Si to Al. In particular embodiments, the molecular sieves suitable herein include those having a Si/Al ratio of about 0.05 to 0.5.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference.

Particular molecular sieves useful in this invention include ZSM-5 (U.S. Pat. Nos. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095) ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein. Other useful molecular sieves include MCM-22, PSH-3, SSZ-25, MCM-36, MCM-49 or MCM-56, with MCM-22. Still other molecular sieves include Zeolite T, ZKS, erionite, and chabazite.

Another option for characterizing a zeolite (or other molecular sieve) is based on the nature of the ring channels in the zeolite. The ring channels in a zeolite can be defined based on the number of atoms included in the ring structure that forms the channel. In some aspects, a zeolite can include at least one ring channel based on a 10-member ring. In such aspects, the zeolite preferably does not have any ring channels based on a ring larger than a 10-member ring. Examples of suitable framework structures having a 10-member ring channel but not having a larger size ring channel include EUO, FER, IMF, LAU, MEL, MFI, MFS, MTT, MWW, NES, PON, SFG, STF, STI, TON, TUN, MRE, and PON.

In some aspects, the catalyst can also optionally include at least one metal selected from Group 8-14 of the Periodic Table, such as at least two metals (i.e., bimetallic) or at least three metals (i.e., trimetallic). Typically, the total weight of the Group 8-14 elements is from about 0.1 to 10 wt. % based on the total weight of the catalyst, preferably from about 0.1 to 2.0 wt. %, and more preferably from about 0.1 to 1.0 wt. %. Of course, the total weight of the Group 8-14 elements shall not include amounts attributable to the molecular sieve itself.

Additionally or alternatively, in some aspects, the catalyst can also include at least one of phosphorous and/or lanthanum and/or other elements from groups 1-2 and/or group 13-16, such as at least two such elements or at least three such elements. Typically, the total weight of the phosphorous and/or lanthanum and/or other elements from groups 1-2 and/or groups 13-16 is about 0.1 to 1.0 wt. % based on the total weight of the catalyst. Of course, the total weight of the phosphorous and/or lanthanum and/or other elements from groups 1-2 and/or groups 13-16 shall not include amounts attributable to the molecular sieve itself.

For the purposes of this description and claims, the numbering scheme for the Periodic Table Groups corresponds to the current IUPAC numbering scheme. Therefore, a "Group 4 metal" is an element from Group 4 of the Periodic Table, e.g., Hf, Ti, or Zr. The more preferred molecular sieves are SAPO molecular sieves, and metal-substituted SAPO molecular sieves. In particular embodiments, one or more Group 1 elements (e.g., Li, Na, K, Rb, Cs, Fr) and/or Group 2 elements (e.g., Be, Mg, Ca, Sr, Ba, and Ra) and/or phosphorous and/or Lanthanum may be used. One or more Group 7-9 element (e.g., Mn, Tc, Re, Fe, Ru, Os, Co, Rh, and Ir) may also be used. Group 10 elements (Ni, Pd, and Pt) are less commonly used in applications for forming olefins and aromatics, as the combination of a Group 10 element in the presence of hydrogen can tend to result in saturation of aromatics and/or olefins. In some embodiments, one or more Group 11 and/or Group 12 elements (e.g., Cu, Ag, Au, Zn, and Cd) may be used. In still other embodiments, one or more Group 13 elements (B, Al, Ga, In, and Tl) and/or Group 14 elements (Si, Ge, Sn, Pb) may be used. In a preferred embodiment, the metal is selected from the group consisting of Zn, Ga, Cd, Ag, Cu, P, La, or combinations thereof. In another preferred embodiment, the metal is Zn, Ga, Ag, or a combination thereof.

Particular molecular sieves and Group 2-13-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (E1APSO where E1 is Be, B, Cr, Co, Ga, Fe, Mg, Mn, Ti, or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti, or Zn), U.S. Pat. No. 4,310,440 (AlPO4), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference. In some aspects, the molecular sieve as modified by the Group 8-14 element and/or a Group 1-2, Group 13-16, lanthanum, and/or phosphorous is a ZSM-5 based molecular sieve.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Patent Application WO 01/36329 published May 25, 2001 (surfactant synthesis), International Patent Application WO 01/25151 published Apr. 12, 2001 (staged acid addition), International Patent Application WO 01/60746 published Aug. 23, 2001 (silicon oil), U.S. Patent Application Publication No. 2002-0055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 2002-0115897 published Aug. 22, 2002 (freeze drying the molecular sieve), which are all herein incorporated by reference in their entirety.

III) Acetylene Formation (Dehydrogenation of Paraffins to Acetylene)

In various aspects, an initial step for conversion of alkynes to aromatics can correspond to providing a suitable source of alkynes. One option for forming an alkyne-containing feedstream can be to perform a dehydrogenation or pyrolysis reaction on an alkane feed to form acetylene, other alkynes, and/or other aliphatic hydrocarbons with multiple degrees of unsaturation such as diolefins.

Several process schemes for conversion of alkanes to alkynes are well-known conventionally. One example of a process flow for formation of acetylene from methane or other alkanes is oxypyrolysis or partial oxidation. In this type of process, methane is burned in a short contact time burner in the presence of oxygen and a suitable catalyst, such as nickel dispersed on an oxide mass. The methane is typically present in a substantial excess relative to the amount of oxygen, such as volume ratio of methane to oxygen of about 70:1 to about 150:1. The methane (or other alkanes) and oxygen streams are heated to an elevated temperature prior to contact in the burner, such as about 200° C. to about 650° C. for a general alkane stream, or about 500° C. to about 650° C. for a natural gas stream. The temperature for pre-heating can be dependent on the amount of impurities present in the respective streams and/or whether any pre-ignition inhibitors are included in the streams to reduce the number of reactions that occur prior to the desired reaction in the short contact time burner.

The temperature in the reaction zone can be above 1500° C. The burner contact time is typically on the order of milliseconds. The resulting product stream is then quenched using a water or oil spray to a temperature below about 220° C. in order to prevent reaction of the acetylene under the severe conditions present in the reaction zone. The short reaction time in the burner can be achieved, for example, by passing the methane and oxygen streams into a reactor at a high space velocity so that the residence time in the reaction zone prior to quenching corresponds to a desired amount. Up to about a third of the methane can be converted to acetylene, while about half can be converted to CO. Excess $H_2$ is also produced, so that the resulting product stream corresponds to a mixture of acetylene and syngas.

The product stream from the partial oxidation reaction can be used directly for production of aromatics, although the hydrogen in the syngas can increase the hydrogen partial pressure during aromatics formation. Optionally, the syngas can be separated from either the feed to the conversion process or the conversion effluent. In this type of aspect, after separation the syngas can be used as an input for another process. If the additional process is a methanol synthesis process, the syngas can be used to make methanol for use in increasing the yield of xylenes in the aromatic conversion process.

Another option for formation of acetylene is conversion of coal to acetylene via formation of calcium carbide as an intermediate product. Rather than starting with paraffins, the alkynes can be derived from coal, such as by converting the coal to coke and then reacting the coke with lime (or another calcium-containing material) at elevated temperatures to form calcium carbide. Calcium carbide can then be reacted with water to produce acetylene. Formation of acetylene from coal via a calcium carbide intermediate product was historically an option for industrial production of acetylene. Formation of acetylene from coal (via a calcium carbide intermediate) can provide a relatively high purity source of acetylene for use in conversion to aromatic compounds.

Still another suitable type of dehydrogenation reaction system for formation of acetylene (by dehydrogenating alkanes to form alkynes) is a reverse flow reaction system. Conversion of alkanes to alkynes is an endothermic process that benefits from elevated temperatures, such as temperatures of 1000° C. or greater. Thus, in addition to initially increasing the temperature of a reaction system to the desired temperature, additional heat needs to be added periodically to replace heat adsorbed by the endothermic reaction. A reverse flow reaction system provides a convenient method for maintaining a desired temperature within a reaction zone while facilitating a desired reaction.

Within the reaction zone of a dehydrogenation reaction system, a feed including alkanes is exposed to a suitable bed of material at elevated temperature. Optionally, the feed can also include hydrogen to reduce or minimize formation of coke within the reaction zone. Such hydrogen addition can be beneficial at higher reaction temperatures, such as the temperatures required for dehydrogenation of methane to alkynes. Preferably, the feed to the dehydrogenation reactor can include at least about 75 vol % of $C_1$ to $C_4$ alkanes, or at least about 75 vol % of $C_1$ to $C_2$ alkanes, or at least about 75 vol % $C_2$ alkanes. The feed to the dehydrogenation reactor can optionally also include a diluent, such as steam or hydrogen. It is noted that at lower temperatures methane can also serve as a diluent.

In addition to alkynes, a dehydrogenation effluent can also contain alkenes, hydrogen, carbon oxides, unreacted paraffins, and various heavier ($C_4$+) non-alkyne compounds. One method for characterizing a product or effluent stream containing alkynes can be based on the ratio of alkynes to alkenes present in the effluent stream. The dehydrogenation conditions that lead to formation of alkynes will typically also result in formation of alkenes to varying degrees. Lower temperatures during a dehydrogenation process can tend to favor formation of alkenes. As the dehydrogenation temperature increases, the ratio of alkynes to alkenes in the dehydrogenation product can also increase.

Small amounts of alkynes can be produced at temperatures of at least 1000° C. in the reaction zone. To achieve a more desirable ratio of alkynes to alkenes, such as a dehydrogenation effluent having a ratio of alkynes to alkenes of at least about 25:75, temperatures of at least about 1100° C. can be used, such as at least about 1200° C. For example, a dehydrogenation product stream containing at least about a 50:50 ratio of acetylene (or other alkynes) to alkenes can be generated using a reaction temperature of at least about 1200° C., or at least about 1250° C., and up to at least about 1350° C. At still higher temperatures, further increases in the ratio of alkynes to alkenes can be achieved, such as a ratio of alkynes to alkenes of about 75:25 or about 90:10. For example, $C_2$+ alkane feeds can be used at temperatures of about 1350° C. to about 1500° C. to achieve a ratio of 75:25, with temperatures above 1400° C. being suitable for a ratio of 90:10. If the alkane feed contains 50 vol % or more of methane, still higher temperatures can be used to generate a dehydrogenation effluent with a 75:25 or 90:10 ratio of alkynes to alkenes, such as temperatures of about 1400° C. to about 1600° C.

U.S. Patent Application Publication 2013/0251608, the entirety of which is incorporated herein by reference, describes an example of a reverse flow reactor configuration suitable for use as a pyrolysis or dehydrogenation reactor. As described in U.S. Patent Application Publication 2013/0251608, the term "reactor" refers to equipment used for chemical conversion. As such, several items identified as reactors may be combined to become a single entity that is also identified as a reactor, in that individual and combined entities may be characterized as equipment used for chemical conversion. The terms "pyrolysis" and "pyrolysis chemistry" mean an endothermic reaction conducted at a temperature sufficient for thermally breaking C—C or C—H bonds, optionally aided by a catalyst, e.g., the conversion of hydrocarbons to unsaturates such as ethylene and acetylene. This type of reaction can also be referred to as a dehydrogenation reaction.

The terms "reactor", "reactor system", "regenerator", "recuperator", "regenerative bed", "monolith", "honeycomb", "reactant", "fuel", and "oxidant" have the meanings disclosed in U.S. Pat. No. 7,943,808, which is incorporated by reference herein in its entirety. The term "pyrolysis reactor", as used herein, refers to a reactor, or combination or system thereof for converting hydrocarbons by at least pyrolysis. A pyrolysis reactor optionally includes one or more reactors and/or associated equipment and lines. The term pyrolysis reactor encompasses, e.g., the combination and system of first and second pyrolysis reactors described in U.S. Patent Application Publication No. 2007/0191664. Other examples are described in U.S. Pat. No. 7,491,250, U.S. Patent Ser. No. 61/349,464 and U.S. Patent Application Publication Nos. 2007/0144940 and 2008/0142409. With respect to pyrolysis reactors, the term "residence time" means the average time duration for non-reacting (non-converting by pyrolysis) molecules (such as He, $N_2$, and Ar) having a molecular weight in the range of 4 to 40 to traverse the reactor or a defined zone within the reactor, such as a pyrolysis zone of a pyrolysis reactor. The term "pyrolysis stage" means at least one pyrolysis reactor, and optionally including means for conducting one or more feeds thereto and/or one or more products away therefrom. With respect to reactors, the term "zone" or "region" means a location within a reactor, e.g., a specific volume within a reactor and/or a specific volume between two reactors. A "pyrolysis zone" is a volume within the reactor for conducting pyrolysis. The term "thermal pyrolysis" means <50.0% of the heat utilized by the pyrolysis is provided by (a) by exothermically reacting an oxidant with hydrocarbon and/or hydrogen of the first mixture, and/or (b) contacting the first mixture with the gaseous and/or liquid products of combustion to heat the first mixture. The term "thermal pyrolysis reactor" means a pyrolysis reactor wherein ≥50.0% of the heat utilized by the pyrolysis is provided by heat transfer from reactor components, e.g., solid surfaces associated with the reactor such as tubulars or bed materials; optionally ≥80.0% or ≥90.0% of the heat utilized by the pyrolysis is provided by such heat transfer. Optionally, an exothermic reaction (e.g., combustion) occurs within the thermal pyrolysis reactor, the exothermic reaction providing a major amount (i.e., ≥50.0%) of the endothermic heat of pyrolysis, such as ≥75.0% or ≥90.0% thereof. The term "high-severity" with respect to the pyrolysis of a feed comprising hydrocarbon, e.g., the first mixture, means pyrolysis operating conditions resulting in the conversion to acetylene of ≥10.0 wt % of the feed's hydrocarbons based on the total weight of hydrocarbons in the feed.

Regenerative pyrolysis reactors are known and conventionally used for converting or cracking reactions, and to execute cyclic, high temperature chemistry, such as those reactions that may be performed at temperatures higher than can suitably be performed in conventional steam crackers. Regenerative reactor cycles typically are either symmetric or asymmetric. Asymmetric cycles are typically used to execute endothermic chemistry, and the desired endothermic chemistry is paired with a different chemistry that is exothermic (typically combustion) to provide heat of reaction for the endothermic reaction. In this embodiment, the regenerative, reverse-flow pyrolysis reactor is (i) "reverse flow" in the sense that upstream region of the reactor with respect to the average flow of the first mixture is the downstream region with respect to the average flow of the fourth mixture, and (ii) "regenerative" in the sense that at least a portion of the heat consumed during the conversion of the first mixture is provided by exothermically reacting the fourth mixture. Regenerative reactor being a reactor that exothermically reacts fuel and oxidant to store heat within a defined volume in a heating step and removes a portion of the heat during the conversion of a feed stream in a conversion step in sequential steps. For example, under thermal pyrolysis conditions, the regenerative reactor exothermically reacts fuel and oxidant to store heat within a defined volume (e.g., reactor bed) in a heating step and removes a portion of the heat during the conversion of a pyrolysis stream in a pyrolysis step.

Accordingly, as it may be appreciated a variety of regenerative pyrolysis reactors may be utilized in accordance with the present techniques. For example, a hydrocarbon pyrolysis reactor may include a housing, a plurality of input means (e.g., conduits and valves), one or more insulation components (e.g., insulation bricks or tiles) and one or more process-flow components (e.g., reactor beds, mixing components, etc.). The housing may be utilized to enclose an interior region and has one or more insulation components disposed adjacent to the housing. The plurality of input means may include one or more conduits and one or more valves that are configured to manage the flow of one or more streams into the interior region from a location external to the interior region or housing. The one or more process-flow components that are configured to manage the flow of fluids through the interior region, wherein the one or more process-flow components may include a reactor bed having different portions with each having different flow passages and a wetted area. These different reactor components may include different compositions based on the process conditions.

Regenerative reverse-flow reactors may involve multiple steps repeated in sequence to form a cycle for the process. During the multiple steps, several different type of feed mixtures can be introduced into the reverse-flow reactor to generate a pyrolysis or dehydrogenation effluent. In the discussion below, a first mixture refers to a hydrocarbon feed that can optionally also contain a diluent, such as a feed of $C_1$ to $C_4$ hydrocarbons as described above. Alternatively, any convenient hydrocarbonaceous feed can be used, including feeds containing various heteroatoms (S, N, O) commonly found in hydrocarbonaceous feeds. References to a second mixture can refer to a pyrolysis or dehydrogenation effluent. References to a fourth mixture can correspond to a mixture of a fuel (e.g., hydrocarbons) and an oxidant (e.g., molecular oxygen) for combustion to provide heat for the reaction zone. References to a fifth mixture can correspond to the products from the combustion reaction that provides heat for the reaction zone.

As an example, a pyrolysis or dehydrogenation process may include two or more sequential steps, which include a regeneration step to heat the zones and a pyrolysis step that converts the hydrocarbons in a first mixture into a second mixture (e.g., reactor products) during a hydrocarbon processing mode. The steps may involve passing mixtures over a solid material in fixed orientation (e.g., one or more reactor beds). As part of these steps, valves may be utilized to alternate introduction of hydrocarbons in a first mixture and/or fourth mixture into the interior region of the reactor. As an example, regenerative reactors typically deliver a fourth mixture (e.g., combustion reactants) of fuel, oxidant, and/or a supplemental amount of one of these reactants, directly to a location along the flow path within the reactor (e.g., a mixing zone). The delivered reactants in the fourth mixture then exothermically react (combust) therein and heat the process-flow components. Thereafter, the fifth mixture (e.g., exothermic reaction products, such as combustion products) is exhausted and a first mixture, such as vaporized hydrocarbons, is introduced into the reactor to flow in the opposite direction, and exposed to the heated process-flow components to cause heating and pyrolysis of the hydrocarbons in the first mixture. The second mixture (e.g., pyrolyzed reaction products and/or unreacted first mixture) is then quenched as they flow through the reactor to halt the pyrolysis reactions and yield pyrolysis products (e.g., reactor products). During the quenching, the process-flow components (e.g., reactor beds) absorb heat from the second mixture, sufficient to impart heat into the fourth mixture when the flow is again reversed.

The high-severity operating conditions may include peak pyrolysis gas temperatures between 1200 and 2200° C., preferably between 1400° C. and 1900° C. In particular, for reactors with an isothermal temperature profile, the temperatures may be between 1450° C. and 1700° C., or between 1540° C. and 1650° C. For reactors with a Gaussian like temperature profile, the peak pyrolysis gas temperatures may be in the range of 1540° C. to 2200° C. or 1600° C. to 1800° C. Further, the preferred operating pressures may include pressures ≥4 pounds per square inch gauge (psig) (28 kilo Pascals gauge (kPag)), ≥15 psig (103 kPag), ≥36 psig (248 kPag), ≥44 psig (303 kPag), or ≥103 psig (710 kPag), but may be ≤300 psig (2068 kPag), ≤163 psig (1124 kPag), or ≤150 psig (1034 kPag). Residence times in the pyrolysis reactor may be ≤0.5 second, ≤0.3 second and preferably ≤about 50 milliseconds or in the range of 0.001 seconds to 1.0 seconds or in the range of 0.5 second and 0.001 second. For a regenerative reactor, the process may operate at cycle times in the range of 1 second to 240 seconds, in the range of 1 second to 60 seconds, in the range of 2 seconds to 40 seconds, in the range of 2 seconds to 20 seconds, or even in the range of 3 seconds to 10 seconds.

Also, as may be appreciated, these different pressures and temperatures may be utilized together to form different combinations depending on the specific configuration of equipment. Further, for a regenerative reverse flow reactor, the pressure in the pyrolysis step may be similar or different to the pressure in the regeneration step (e.g., at lower or higher pressure than the pyrolysis step).

The regeneration step has different temperature profiles along the flow path at different locations within the reactor for each of the steps. The shape of that profile depends on many factors, including if and where a heat release reaction (combustion) occurs, the initial temperature distribution, the duration of the regeneration step, the flow rate and inlet temperature of the gas stream, and the heat capacity and transfer properties of the gas and solid material. On average, the solid material is hottest at the end of the regeneration step. The pyrolysis step consumes heat and reduces average solid material temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors do not operate in the steady state. That is, at any given location, the temperature changes. However, these reactors may be in a periodic steady state, meaning that the same cycling of temperatures occurs over and over as the reactor sequentially repeats the regeneration and pyrolysis steps.

IV) Process Flow Examples—Alkynes to Aromatics

Figure 2:
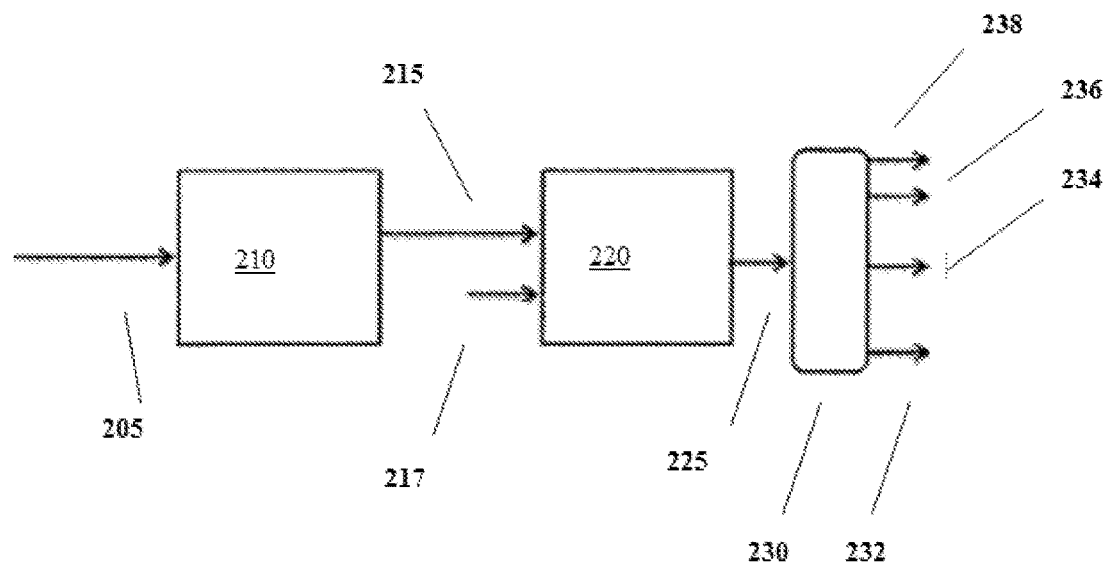
FIG. 2 schematically shows an example of a reaction system for forming alkynes via dehydrogenation and converting alkynes, alkenes, and/or methanol to form aromatics.

FIG. 2 schematically shows an example of a reaction system for conversion of alkynes and alkenes and/or methanol to aromatics. In the reaction system shown in FIG. 2, a reactor (such as a regenerative flow reactor) is used to dehydrogenate an alkane feed to form a mixture of alkynes and alkenes. Optionally, to facilitate formation of xylenes, methanol can be added as a co-feed.

As shown in FIG. 2, an initial alkane (ethane) feed 205 is introduced into a dehydrogenation reactor (such as a regenerative flow reactor) 210. Optionally, either prior to or after entry into reactor 210, the alkane feed 205 can be combined with a recycled portion of the effluent from the conversion reaction. Under reaction conditions where a substantial number of alkenes are used to form aromatics, a substantial amount of alkanes may be produced as part of the effluent from the conversion reaction. Such alkanes can be recycled back to the dehydrogenation reaction for conversion to alkynes or alkenes.

The reactor 210 can be operated under effective dehydrogenation conditions. The dehydrogenation effluent 215 from reactor 210 can correspond to a mixture of alkynes, alkenes, unreacted alkanes (optionally including methane), and excess hydrogen. The dehydrogenation effluent 215 (or at least a portion thereof) can be introduced into a conversion reactor 220 for conversion of the alkynes and optionally alkenes to aromatics. Either prior to or after entry into conversion reactor 220, a co-feed of methanol 217 can optionally be added to the dehydrogenation effluent 215. After formation of aromatics in the conversion reactor 220, the conversion effluent 225 can be separated 230 to generate various product streams, including an aromatics product stream 232, an ethylene product stream 234, one or more alkane streams 236, and a stream containing potential fuel products, such as $H_2$ and/or optionally methane. If recycled alkanes are used as part of the feed to reactor 210, at least a portion of the alkane stream(s) 236 can be used as the recycled alkanes. Optionally but preferably, the aromatics product stream 442 can be a para-xylene rich stream.

Figure 4:
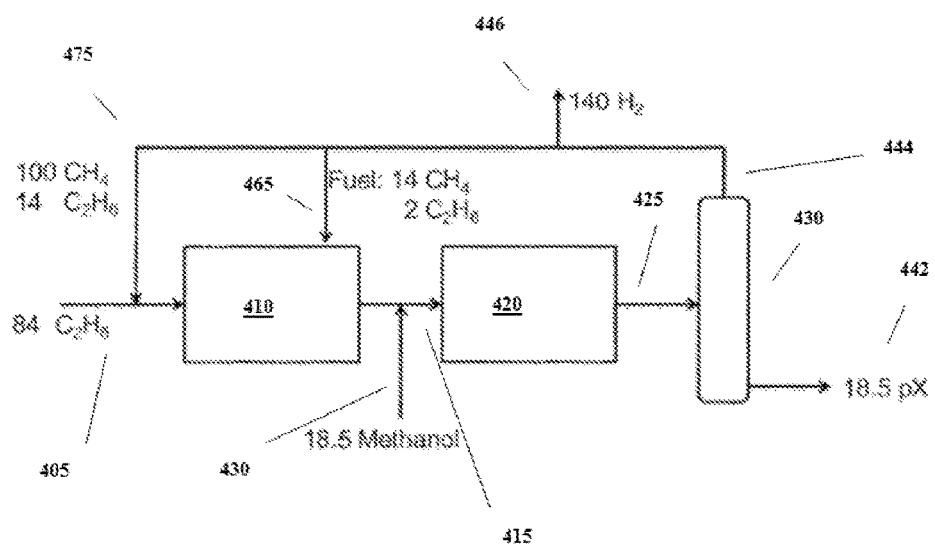
FIG. 4 schematically shows an example of a reaction system for forming alkynes via dehydrogenation and converting alkynes, alkenes, and/or methanol to form aromatics.

FIG. 4 schematically shows another example of a process flow sheet for conversion alkynes and alkenes to aromatics. In the flow sheet shown in FIG. 4, a regenerative flow reactor is used to dehydrogenate an alkane feed (ethane) to form an about 50:50 mixture of alkynes and alkenes. To facilitate formation of xylenes, methanol is added as a co-feed.

As shown in FIG. 4, an initial ethane feed 405 is introduced into a dehydrogenation reactor (such as a regenerative flow reactor) 410. Either prior to or after entry into reactor 410, the ethane feed 405 can be combined with a recycled paraffin feed 475. The recycled paraffin feed 475 is shown as a combination of methane and ethane in FIG. 4, but other paraffins can also be included. Fuel stream 465 for maintaining the temperature of the reactor 410 can correspond to a portion of the recycled feed 475. The reactor 410 can be operated under effective dehydrogenation conditions. For generation of a 50:50 mixture of alkynes and alkenes from an ethane feed, the effective dehydrogenation conditions in reactor 410 can correspond to the lower range of dehydrogenation temperatures, such as a temperature from about 1250° C. to about 1350° C. It is noted that under these reaction conditions, the methane from recycled paraffin feed 475 can serve largely as a diluent within the reactor 410, as the reaction temperatures are not sufficiently high to dehydrogenate a substantial portion of the methane.

The dehydrogenation effluent 415 from reactor 410 can correspond to a mixture of alkynes, alkenes, unreacted alkanes (including methane), and excess hydrogen. The dehydrogenation effluent 415 (or at least a portion thereof) can be introduced into a conversion reactor 420 for conversion of the alkynes and alkenes to aromatics. Either prior to or after entry into conversion reactor 420, a co-feed of methanol 430 can be added to the dehydrogenation effluent 415. After formation of aromatics in the conversion reactor 420, the conversion effluent 425 can be separated 430 to generate a product stream of aromatics 442. Optionally but preferably, the aromatics product stream 442 can be a para-xylene rich stream. A light gases stream 444 can also be formed that includes hydrogen, any remaining alkenes or alkynes, and light paraffins. A hydrogen stream 446 can be separated from light gases stream 444. The remaining portion of the light gases stream 444 can be used either as recycled paraffin feed 475 or fuel stream 465. It is noted that if fuel stream 465 is not formed from the light gases stream 444 prior to use as a recycled feed, a separate bleed stream can be removed from the light gases stream (not shown) to prevent accumulation of methane in the recycle loop.

In addition to providing an example of a process flow, FIG. 4 also shows an example of the molar balance for the various reactants in the reaction system when the reaction is operated to generate a roughly 1:1 molar ratio of acetylene to ethylene in dehydrogenation reactor 420. The relative molar quantities shown in FIG. 4 represent the components in the reaction system that have a substantial concentration. It is noted that under the reaction conditions used for generating the molar balance in FIG. 4, the dehydrogenation reactor produced about a 1:1 molar ratio of acetylene to ethylene, with about 7 mol % methane and about 13 mol % C3+ compounds (not shown) also being produced. In the conversion reaction, more than 50 wt. % of the ethylene introduced into the reactor is consumed during the reaction. Some of the ethylene consumed can be used in combination with acetylene to arrive at the correct hydrogen to carbon ratio for formation of para-xylene (or other desired aromatics). The remaining portion of the ethylene consumed in the reaction is used to make additional aromatics. Because the remaining portion of ethylene used for formation of aromatics has a hydrogen to carbon ratio that is greater than the hydrogen to carbon ratio of various aromatics, the reaction products from the conversion reaction also include ethane and $H_2$ as products in addition to the aromatics. The ethane and $H_2$ products are high hydrogen to carbon ratio products that allow the hydrogen to carbon ratio of the products to match the starting hydrogen to carbon ratio of the ethylene.

As an alternative to recycling the light gases stream 444, a more refined separation can be performed to allow additional product streams to be generated. For example, the methane and hydrogen generated from the conversion reaction can be separated out in one or more product streams for use as a fuel or as an input to another process. Similarly, rather than recycling the ethylene, which has a lower reactivity, the ethylene can also be withdrawn from the reaction system as a product. Larger paraffin compounds ($C_2+$) can still be used as a recycle stream, as the $C_2+$ paraffins are suitable for dehydrogenation under the milder conditions used for formation of a 50:50 ratio of alkynes to alkenes.

If more severe dehydrogenation reaction conditions are used in reactor 410, such as temperatures of at least about 1400° C., the ratio of alkynes to alkenes in the dehydrogenation effluent 415 can be increased to achieve a higher proportion of alkynes to alkenes, such as a 75:25 ratio or a 90:10 ratio. More severe dehydrogenation conditions do not change the subsequent conversion reaction directly, although the more severe dehydrogenation conditions can modify the feed that is delivered to the conversion reaction. For example, if the dehydrogenation reactor 410 has a sufficiently high temperature, methane in the input feed 405 to the dehydrogenation reactor 410 can also be dehydrogenated to form alkynes and alkenes.

Figure 5:
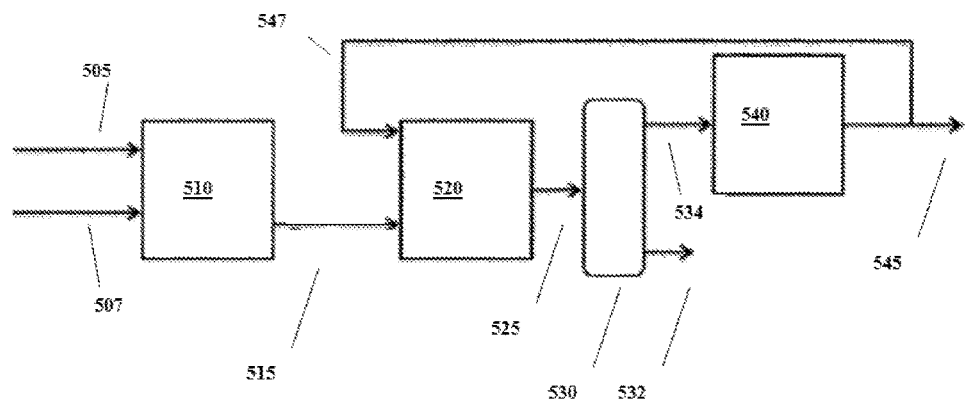
FIG. 5 schematically shows an example of a reaction system for forming alkynes via partial oxidation and converting alkynes and optionally methanol to form aromatics.

FIG. 5 shows another process flow for formation of aromatics from methane or other light alkanes. In the process flow in FIG. 5, a methane feed 505 is introduced into a partial oxidation reactor 510 along with an oxygen feed 507. The resulting dehydrogenated product stream 515 from the partial oxidation reactor 510 corresponds to a mixture of acetylene and syngas. The dehydrogenated product stream 515 can then be passed into a conversion reactor 520. Optionally but preferably, a co-feed 547 of methanol can also be introduced as described above. The resulting conversion effluent 525 can then be separated 530 to form at least an aromatics product 532 and a syngas product stream 534. In the configuration shown in FIG. 5, the syngas product stream can be used as a feed for a methanol synthesis reactor 540. A portion of the methanol output 545 from the methanol synthesis reactor 540 can be used as the methanol co-feed 547. Alternatively, the syngas can be used for any other convenient fuel and/or synthesis purpose.

V) Alternative Feeds—Conversion of Mixtures of Oxygenates and Olefins

Another option for formation of aromatic compounds is to use methanol as the primary feed for a conversion reaction. In conventional methanol to olefin processes, the conversion conditions have some tendency to cause formation of $C_9$ or $C_{10}$ aromatics, such as durene. Due in part to the less favorable volatility properties of durene, reducing or minimizing the amount of $C_9+$ aromatics formed during synthesis of gasoline can be desirable.

One option for reducing or minimizing the amount of $C_9+$ aromatics can be to add a co-feed of $C_3$ to $C_{10}$ olefins, such as a co-feed of $C_4$ to $C_7$ olefins, or a co-feed of $C_3$ to $C_5$ olefins. One way for characterizing the amount of methanol or other oxygenate relative to the amount of olefins can be based on the relative amount of carbon in each feed component. In various aspects, a ratio of moles of carbon in the oxygenate portion of the feed to moles of carbon in the olefin portion of the feed can range from about 95:5 to 10:90. For example, the ratio of moles of carbon in the oxygenate portion of the feed to moles of carbon in the olefin portion of the feed can be about 5.5:1 or less, or about 5:1 or less, or about 4:1 or less, or about 3:1 or less, or at least about 1:9, or at least about 1:5, or at least about 1:3, or at least about 1:2. Each of the upper and lower bounds for the ratio of moles of carbon in the oxygenate portion of the feed relative to the moles of carbon in the olefin portion of the feed is explicitly contemplated in conjunction with each other. The reaction conditions and catalysts suitable for conversion to aromatics (or gasoline) when using an olefin co-feed can be similar to the reaction conditions/catalysts for conversion of oxygenates to aromatics (or gasoline), as described above.

The feed containing oxygenates and olefins can be converted to aromatics by exposing the feed to an aromatization catalyst (as described above) under effective conversion conditions. Conversion conditions can include general conversion conditions as described above. Alternatively, for conversion of a feed of oxygenates and olefins to form a product with a reduced or minimized amount of $C_9+$ aromatics, the conditions can include a pressure of about 100 kPaa to about 7000 kPaa, or about 100 kPaa to about 2000 kPaa, or about 100 kPaa to about 1500 kPaa, or about 100 kPaa to about 1200 kPaa. The temperature can be about 350° C. to about 700° C., or about 400° C. to about 700° C., or about 350° C. to about 600° C., or about 300° C. to about 450° C., or about 400° C. to about 600° C. The amount of feed (weight) relative to the amount of catalyst (weight) can be expressed as a weight hourly space velocity (WHSV). Suitable weight hourly space velocities include a WHSV of about 0.1 $hr^{-1}$ to about 20 $hr^{-1}$, or about 1.0 $hr^{-1}$ to about 10 $hr^{-1}$.

To demonstrate the benefits of using an olefin co-feed, a methanol to gasoline conversion reaction was performed using a bound ZSM-5 catalyst that also included 1.2 wt. % of phosphorous supported on the catalyst. The ZSM-5 catalyst was used to convert a methanol feed and a mixture of methanol and 2-pentene having a 50:50 ratio of carbon in the methanol to carbon in the 2-pentene.

For the conversion reaction, the ZSM-5 catalyst was sized to a particle size of 0.7 mm to 1.4 mm. Two grams of the catalyst were then mixed with quartz particles of a similar size in a ratio of approximately 1:3. The catalyst was loaded into a plug flow reactor and exposed to the methanol or methanol/pentene feeds at 450° C. and 15 psig.

The methanol feed corresponded to 99.92% methanol. The methanol and 2-pentene feed was a mixture of methanol and 99% 2-pentene (mixture of cis and trans) with a 50:50 carbon ratio as described above. This resulted in a mixture of methanol and 2-pentene with a density of about 0.7454 g/ml. The methanol feed was exposed to the ZSM-5 catalyst at a weight hourly space velocity (WHSV) of 2 $hr^{-1}$. This process run may be referred to below and in the figures as Experiment A. The mixture of methanol and 2-pentene was exposed to the ZSM-5 catalyst at two different space velocities. In a first type of process run with the methanol/2-pentene mixture, a WHSV of 2 $hr^{-1}$ was used (Experiment B) to provide a comparison at constant space velocity. In a second type of process run, the space velocity for the mixture of methanol and 2-pentene was selected to have the same "velocity" of moles of carbon as the methanol feed. Due to the higher carbon density of 2-pentene relative to methanol, a WHSV of 1.44 $hr^{-1}$ (Experiment C) for the mixture of methanol and 2-pentene corresponded to passing the same moles of carbon per hour to the catalyst as the methanol feed at a WHSV of 2 $hr^{-1}$.

The liquid product obtained after 18 hours of processing was characterized for density and carbon yield. The density was measured in grams per milliliter. The "yield" was characterized based on the mass of the liquid hydrocarbon product relative to the mass of $CH_2$ units in the feed. The liquid product included a top phase of aromatic compounds and a bottom phase of paraffins and olefins.

For a methanol only feed at a WHSV of 2 $hr^{-1}$ (Experiment A), the density of the resulting total liquid hydrocarbon product was about 0.8267 g/ml with a yield of about 44.6% based on the yield definition provided above. For the methanol/2-pentene mixture at the WHSV of 2 $hr^{-1}$ (Experiment B), two separate runs gave similar results. A first run with the mixed feed at the WHSV of 2 $hr^{-1}$ resulted in a density of about 0.8268 g/ml and a yield of 43.4%, while a second run resulted in a density of about 0.8210 g/ml and a yield of 44.9%. This demonstrates that the overall yield was similar for both the pure methanol feed and the mixed methanol/2-pentene feed at constant space velocity. By contrast, for the mixed methanol/2-pentene feed at a space velocity of 1.44 $hr^{-1}$ (Experiment C) selected to provide a similar carbon flux to the pure methanol feed, the density of the total liquid hydrocarbon product was about 0.8473 g/ml while the yield was about 35%. Thus, providing a similar total carbon flux relative to a methanol feed resulted in a lower yield and a change in the composition of the total liquid hydrocarbon product.

Figure 6:
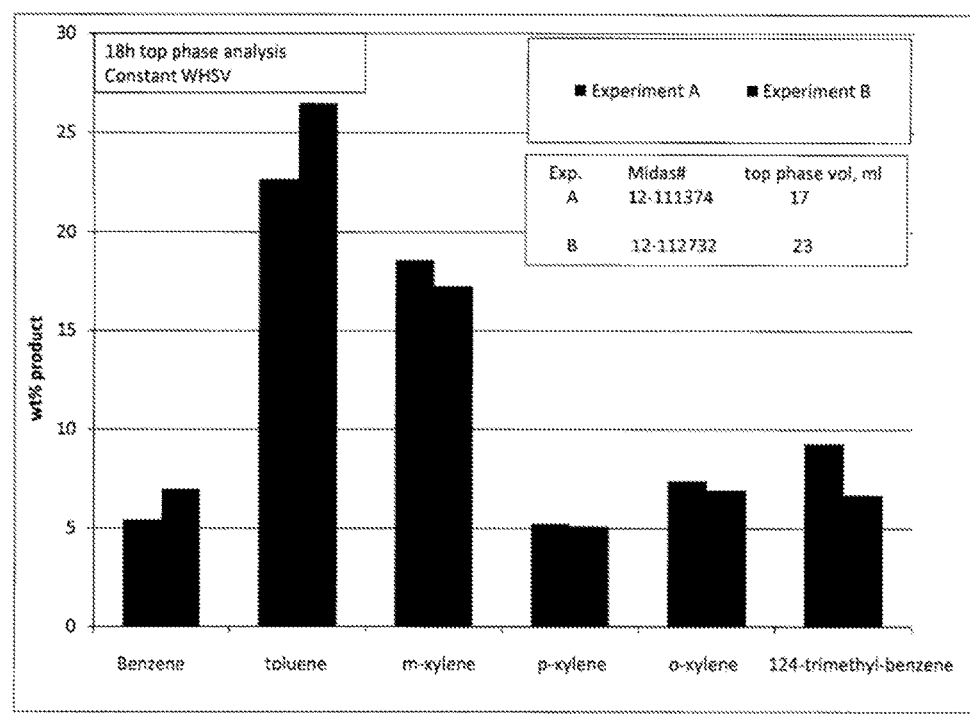
FIG. 6 shows selectivity for formation of various products during conversion of methanol to aromatics optionally in the presence of a pentene co-feed.
Figure 7:
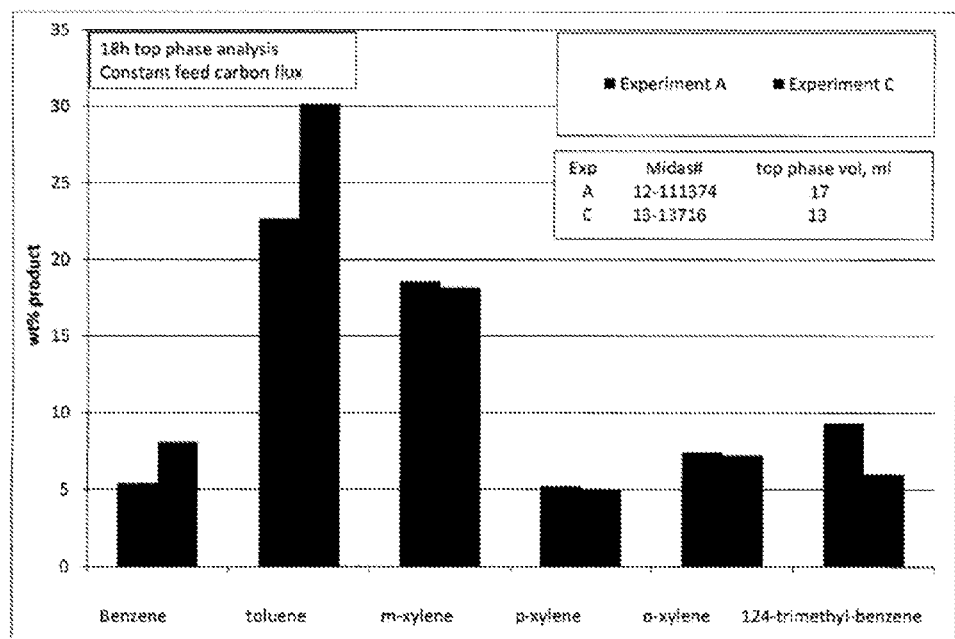
FIG. 7 shows selectivity for formation of various products during conversion of methanol to aromatics optionally in the presence of a pentene co-feed.

To further characterize the results, the top phase (aromatics) from the process runs described above was characterized to determine the product selectivity. FIG. 6 shows a comparison of the aromatics selectivity for the process runs corresponding to Experiment A and Experiment B. In the bar chart shown in FIG. 6, the left hand bar in each data pair corresponds to Experiment A, while the right hand bar corresponds to Experiment B. This is further labeled for several of the data pairs in FIG. 6. As shown in FIG. 6, using a mixed methanol/2-pentene feed resulted in a higher selectivity for benzene and toluene (relative to a pure methanol feed), a similar selectivity for xylene, and a lower selectivity for 1,2,4-trimethyl benzene. This shows that use of a pentene co-feed reduced the formation of more highly substituted aromatics. FIG. 7 provides a similar comparison in aromatics selectivity for Experiment A and Experiment C. As shown in FIG. 7, a similar increase in benzene and toluene selectivity at the expense of 1,2,4-trimethyl benzene was observed.

Figure 8:
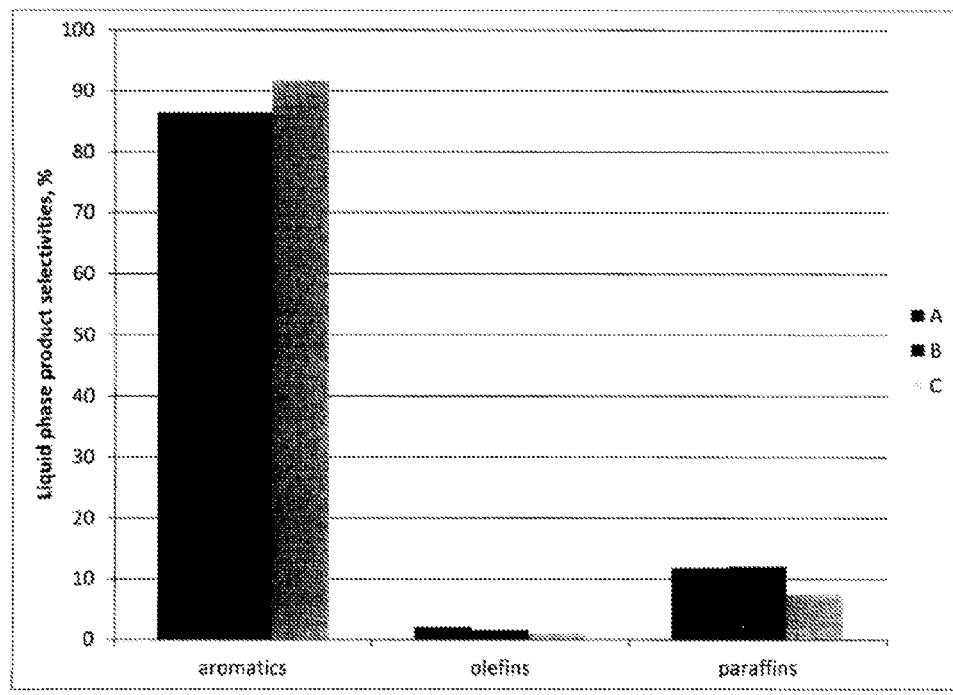
FIG. 8 shows selectivity for formation of various products during conversion of methanol to aromatics optionally in the presence of a pentene co-feed.

FIG. 8 shows the total liquid hydrocarbon selectivity for Experiments A, B, and C. The total liquid hydrocarbon product was characterized based on the categories of aromatics, olefins, and paraffins. As shown in FIG. 8, the relative amounts of aromatics, olefins, and paraffins are similar for Experiments A and B, which were performed at similar space velocities. However, Experiment C generated a different product mix, with increased aromatics selectivity at the expense of reduced formation of paraffins. This shift in the product mixture accounted at least in part for the increased density observed for the total liquid product in Experiment C.

Figure 9:
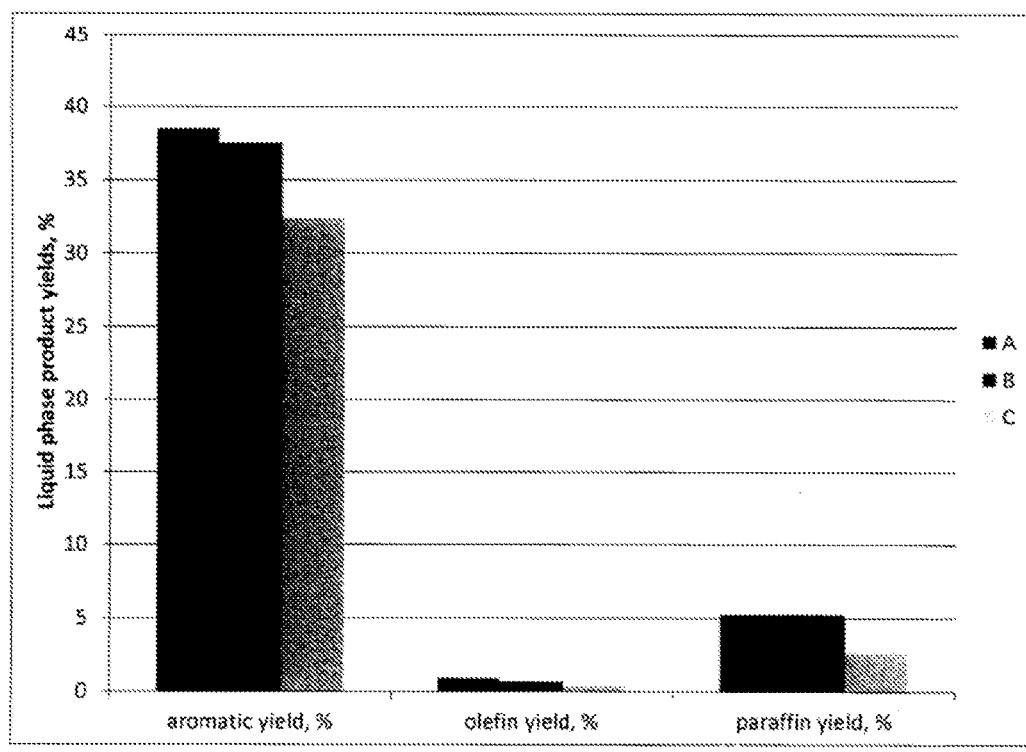
FIG. 9 shows selectivity for formation of various products during conversion of methanol to aromatics optionally in the presence of a pentene co-feed.

Although the aromatics selectivity for Experiment C is greater than the selectivity in Experiment A or B, the total aromatic yield in Experiment C is still lower. FIG. 9 shows the liquid hydrocarbon yields (calculated as described above) for aromatics, olefins, and paraffins for Experiments A, B, and C. As shown in FIG. 9, although the aromatics selectivity is greater for Experiment C, the total yield of aromatics is still lower.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention. Ranges disclosed herein include combinations of any of the enumerated values.

What is claimed is:

1. A method for forming aromatic compounds, comprising:
    dehydrogenating a feed comprising at least about 75 vol % ethane, under dehydrogenation conditions to form a dehydrogenation effluent containing at least about 25 vol % alkynes and wherein at least some of the alkynes comprise acetylene, the dehydrogenation conditions including a temperature of at least about 1000° C.; and converting at least a portion of the dehydrogenation effluent under effective conversion conditions with an aromatization catalyst to form a conversion effluent comprising a hydrocarbon product containing aromatic compounds, wherein a volume percentage of aromatic compounds in the hydrocarbon product are at least about 10 vol % greater than a volume percentage of aromatic compounds in the dehydrogenation effluent, and wherein a molar ratio of acetylene to methanol provided to the aromatization catalyst is 5:1 or less, wherein the converting comprises reacting methanol molecules with acetylene molecules to form methyl acetylene, and reacting an additional acetylene with the methyl acetylene to form para-xylene.

2. The method of claim 1, wherein dehydrogenating the feed comprises dehydrogenating the feed in a reverse flow reaction system.

3. The method of claim 1, wherein the effective conversion conditions comprise exposing the dehydrogenation effluent to a molecular sieve at a temperature of about 300° C. to about 700° C. and a total pressure of about 100 kPag to about 7000 kPag.

4. The method of claim 1, wherein the aromatization catalyst is selectivated to enhance yield of para-xylene.

5. The method of claim 1, wherein the dehydrogenation conditions comprise partial oxidation conditions.

6. The method of claim 5, wherein the dehydrogenation effluent also comprises $H_2$ and CO, the method further comprising:

separating the dehydrogenation effluent to form a syngas-enriched stream having a greater concentration of $H_2$ and CO than the dehydrogenation effluent, and an acetylene-enriched stream having a greater concentration of acetylene than the dehydrogenation effluent; and exposing the syngas-enriched stream to effective conditions for formation of methanol to form a methanol-containing stream;

wherein the converting comprises feeding at least a portion of the acetylene-enriched stream and at least a portion of the methanol-containing stream to the aromatization catalyst to form a second conversion effluent.

7. The method of claim 1, wherein the dehydrogenation conditions comprise pyrolysis conditions.

8. The method of claim 7, wherein the dehydrogenation effluent has a ratio of alkynes to alkenes of about 1:2 to about 2:1.

9. The method of claim 7, wherein the dehydrogenation effluent has a ratio of alkynes to alkenes of at least about 3:1.

10. The method of claim 1, wherein less than about 50 wt. % of the alkenes present in the feed are reacted under the conversion conditions.

11. The method of claim 1, wherein the aromatization catalyst comprises ZSM-5 and at least one Group 8-14 element.

* * * * *